(12) United States Patent
Shaquer et al.

(10) Patent No.: US 12,250,522 B2
(45) Date of Patent: Mar. 11, 2025

(54) LIGHT DRIVEN CONTACT HEARING AID

(71) Applicant: Earlens Corporation, Menlo Park, CA (US)

(72) Inventors: Cem Shaquer, Saratoga, CA (US); Louis Wong, Los Altos Hills, CA (US); Kin Chan, Los Gatos, CA (US); Paul Rucker, San Francisco, CA (US)

(73) Assignee: Earlens Corporation, Menlo Park, CA (US)

( * ) Notice: Subject to any disclaimer, the term of this patent is extended or adjusted under 35 U.S.C. 154(b) by 1119 days.

(21) Appl. No.: 16/933,323

(22) Filed: Jul. 20, 2020

(65) Prior Publication Data

US 2020/0351600 A1    Nov. 5, 2020

Related U.S. Application Data

(63) Continuation of application No. PCT/US2019/013822, filed on Jan. 16, 2019.
(Continued)

(51) Int. Cl.
*H04R 25/00* (2006.01)
*A61B 5/00* (2006.01)
(Continued)

(52) U.S. Cl.
CPC ......... *H04R 25/606* (2013.01); *A61B 5/6817* (2013.01); *A61F 2/18* (2013.01);
(Continued)

(58) Field of Classification Search
CPC .... H04R 25/554; H04R 23/008; A61B 5/6817
See application file for complete search history.

(56) References Cited

U.S. PATENT DOCUMENTS

| 4,375,016 A | 2/1983 | Harada |
| 4,747,656 A | 5/1988 | Miyahara et al. |

(Continued)

FOREIGN PATENT DOCUMENTS

| DE | 3508830 A1 | 9/1986 |
| KR | 100624445 B1 | 9/2006 |

(Continued)

OTHER PUBLICATIONS

Dundas et al. The Earlens Light-Driven Hearing Aid: Top 10 questions and answers. Hearing Review. 2018;25(2):36-39.
(Continued)

*Primary Examiner* — Carrie R Dorna
(74) *Attorney, Agent, or Firm* — Polsinelli PC (57) ABSTRACT

The present invention is directed to a contact hearing system utilizing an emitter adapted to emit light and a contact hearing device adapted to receive the emitted light and convert that light into sound by mechanical manipulation of a subjects ear drum. In the present invention the emitter may utilize multiple light sources and the multiple light sources may be passed through at least one diffuser in order to generate an emitted light having a broader angle of incidence with little or no loss in received power as measured by a photodetector on the contact hearing device when the contact hearing device is positioned on a subject's tympanic membrane and the emitter is positioned in the subject's ear canal.

18 Claims, 10 Drawing Sheets

Related U.S. Application Data (60) Provisional application No. 62/620,341, filed on Jan. 22, 2018.

(51) Int. Cl.
*A61F 2/18* (2006.01)
*H01S 5/00* (2006.01)

(52) U.S. Cl.
CPC ......... *H04R 25/554* (2013.01); *H04R 25/603* (2019.05); *A61F 2002/183* (2013.01); *H01S 5/005* (2013.01)

(56) References Cited

U.S. PATENT DOCUMENTS

| | | | |
|---|---|---|---|
| 5,259,032 A | 11/1993 | Perkins et al. | |
| 5,624,376 A | 4/1997 | Ball et al. | |
| 5,804,109 A | 9/1998 | Perkins | |
| 6,068,589 A | 5/2000 | Neukermans | |
| 6,137,889 A | 10/2000 | Shennib et al. | |
| 6,190,305 B1 | 2/2001 | Ball et al. | |
| 6,473,512 B1 | 10/2002 | Juneau et al. | |
| 6,491,644 B1 | 12/2002 | Vujanic et al. | |
| 6,724,902 B1 | 4/2004 | Shennib et al. | |
| 6,931,231 B1 | 8/2005 | Griffin | |
| 6,940,989 B1 | 9/2005 | Shennib et al. | |
| 7,095,981 B1 | 8/2006 | Voroba et al. | |
| 7,289,639 B2 | 10/2007 | Abel et al. | |
| 7,627,131 B2 | 12/2009 | Nielsen et al. | |
| 7,630,646 B2 | 12/2009 | Anderson et al. | |
| 7,983,435 B2 | 7/2011 | Moses | |
| 8,116,494 B2 | 2/2012 | Rass | |
| 8,157,730 B2 | 4/2012 | LeBoeuf et al. | |
| 8,194,911 B2 | 6/2012 | Dyer et al. | |
| 8,204,786 B2 | 6/2012 | LeBoeuf et al. | |
| 8,251,903 B2 | 8/2012 | LeBoeuf et al. | |
| 8,320,982 B2 | 11/2012 | LeBouef et al. | |
| 8,396,239 B2 | 3/2013 | Fay et al. | |
| 8,512,242 B2 | 8/2013 | LeBoeuf et al. | |
| 8,545,383 B2 | 10/2013 | Wenzel et al. | |
| 8,600,089 B2 | 12/2013 | Wenzel et al. | |
| 8,647,270 B2 | 2/2014 | LeBoeuf et al. | |
| 8,652,040 B2 | 2/2014 | LeBoeuf et al. | |
| 8,700,111 B2 | 4/2014 | LeBoeuf et al. | |
| 8,702,607 B2 | 4/2014 | LebBoeuf et al. | |
| 8,715,152 B2 | 5/2014 | Puria et al. | |
| 8,761,423 B2 | 6/2014 | Wagner et al. | |
| 8,788,002 B2 | 7/2014 | LeBoeuf et al. | |
| 8,885,860 B2 | 11/2014 | Djalilian et al. | |
| 8,886,269 B2 | 11/2014 | LeBoeuf et al. | |
| 8,888,701 B2 | 11/2014 | LeBoeuf et al. | |
| 8,923,941 B2 | 12/2014 | LeBoeuf et al. | |
| 8,929,965 B2 | 1/2015 | LeBoeuf et al. | |
| 8,929,966 B2 | 1/2015 | LeBoeuf et al. | |
| 8,934,952 B2 | 1/2015 | LeBoeuf et al. | |
| 8,942,776 B2 | 1/2015 | LeBoeuf et al. | |
| 8,961,415 B2 | 2/2015 | LeBoeuf et al. | |
| 8,989,830 B2 | 3/2015 | LeBoeuf et al. | |
| 9,044,180 B2 | 6/2015 | LeBoeuf et al. | |
| 9,131,312 B2 | 9/2015 | LeBoeuf et al. | |
| 9,289,135 B2 | 3/2016 | LeBoeuf et al. | |
| 9,289,175 B2 | 3/2016 | LeBoeuf et al. | |
| 9,301,696 B2 | 4/2016 | LeBoeuf et al. | |
| 9,314,167 B2 | 4/2016 | LeBoeuf et al. | |
| 9,392,377 B2 | 7/2016 | Olsen et al. | |
| 9,427,191 B2 | 8/2016 | LeBoeuf | |
| 9,521,962 B2 | 12/2016 | LeBoeuf | |
| 9,538,921 B2 | 1/2017 | LeBoeuf et al. | |
| 9,750,462 B2 | 9/2017 | LeBoeuf et al. | |
| 9,788,785 B2 | 10/2017 | LeBoeuf | |
| 9,788,794 B2 | 10/2017 | LeBoeuf et al. | |
| 9,791,639 B2 | 10/2017 | Zhao et al. | |
| 9,794,653 B2 | 10/2017 | Aumer et al. | |
| 9,801,552 B2 | 10/2017 | Romesburg | |
| 9,808,204 B2 | 11/2017 | LeBoeuf et al. | |
| 10,306,381 B2 | 5/2019 | Sandhu et al. | |
| 2006/0161255 A1 | 7/2006 | Zarowski et al. | |
| 2009/0052706 A1 | 2/2009 | Gottschalk et al. | |
| 2009/0304216 A1 | 12/2009 | Hansen et al. | |
| 2010/0034409 A1* | 2/2010 | Fay | H04R 25/554 |
| | | | 381/326 |
| 2010/0166241 A1 | 7/2010 | Sabio | |
| 2011/0268308 A1 | 11/2011 | Vasquez | |
| 2011/0295331 A1* | 12/2011 | Wells | A61N 5/0601 |
| | | | 607/3 |
| 2012/0051578 A1 | 3/2012 | Parkins et al. | |
| 2012/0097475 A1 | 4/2012 | Schumaier | |
| 2012/0099823 A1 | 4/2012 | Wu et al. | |
| 2013/0016861 A1 | 1/2013 | Kaempf | |
| 2013/0023962 A1 | 1/2013 | Stafford et al. | |
| 2013/0034258 A1 | 2/2013 | Lin | |
| 2013/0161119 A1 | 6/2013 | Mulvey | |
| 2013/0294630 A1 | 11/2013 | Matsuo et al. | |
| 2014/0153768 A1 | 6/2014 | Hagen et al. | |
| 2015/0146900 A1 | 5/2015 | Vonlanthen et al. | |
| 2015/0222978 A1 | 8/2015 | Murozaki | |
| 2015/0245131 A1 | 8/2015 | Facteau et al. | |
| 2015/0358749 A1 | 12/2015 | Karamuk et al. | |
| 2016/0066110 A1 | 3/2016 | Shennib et al. | |
| 2016/0173971 A1 | 6/2016 | Lott et al. | |
| 2016/0330555 A1 | 11/2016 | Vonlanthen et al. | |
| 2018/0048970 A1 | 2/2018 | Demartini et al. | |
| 2019/0166438 A1 | 5/2019 | Perkins et al. | |
| 2019/0174240 A1 | 6/2019 | Johnson et al. | |
| 2020/0137503 A1 | 4/2020 | Demartini et al. | |
| 2020/0267485 A1 | 8/2020 | Perkins et al. | |

FOREIGN PATENT DOCUMENTS

| | | |
|---|---|---|
| WO | WO-2018035036 A1 | 2/2018 |
| WO | WO-2019143702 A1 | 7/2019 |

OTHER PUBLICATIONS

Fay, et al. Preliminary evaluation of a light-based contact hearing device for the hearing impaired. Otol Neurotol. Jul. 2013;34(5):912-21. doi: 10.1097/MAO.0b013e31827de4b1.

Fritsch, et al. EarLens transducer behavior in high-field strength MRI scanners. Otolaryngol Head Neck Surg. Mar. 2009; 140(3):426-8. doi: 10.1016/j.otohns.2008.10.016.

Gantz, et al. Broad Spectrum Amplification with a Light Driven Hearing System. Combined Otolaryngology Spring Meetings, 2016 (Chicago).

Gantz, et al. Light Driven Hearing System: A Multi-Center Clinical Study. Association for Research in Otolaryngology Annual Meeting, 2016 (San Diego).

Gantz, et al. Light-Driven Contact Hearing Aid for Broad Spectrum Amplification: Safety and Effectiveness Pivotal Study. Otology & Neurotology Journal, 2016 (in review).

Gantz, et al. Light-Driven Contact Hearing Aid for Broad-Spectrum Amplification: Safety and Effectiveness Pivotal Study. Otology & Neurotology. Copyright 2016. 7 pages.

International search report with written opinion dated Mar. 26, 2019 for PCT/US2019/013822.

Jian, et al. A 0.6 V, 1.66 mW energy harvester and audio driver for tympanic membrane transducer with wirelessly optical signal and power transfer. InCircuits and Systems (ISCAS), 2014 IEEE International Symposium on Jun. 1, 2014. 874-7. IEEE.

Khaleghi, et al. Attenuating the ear canal feedback pressure of a laser-driven hearing aid. J Acoust Soc Am. Mar. 2017; 141(3):1683.

Khaleghi, et al. Attenuating the feedback pressure of a light-activated hearing device to allows microphone placement at the ear canal entrance. IHCON 2016, International Hearing Aid Research Conference, Tahoe City, CA, Aug. 2016.

Khaleghi, et al. Characterization of Ear-Canal Feedback Pressure due to Umbo-Drive Forces: Finite-Element vs. Circuit Models. ARO Midwinter Meeting 2016, (San Diego).

Khaleghi, et al. Mechano-Electro-Magnetic Finite Element Model of a Balanced Armature Transducer for a Contact Hearing Aid. Proc. MoH 2017, Mechanics of Hearing workshop, Brock University, Jun. 2017.

(56) References Cited

OTHER PUBLICATIONS

Khaleghi, et al. Multiphysics Finite Element Model of a Balanced Armature Transducer used in a Contact Hearing Device. ARO 2017, 40th ARO MidWinter Meeting, Baltimore, MD, Feb. 2017.
Lee, et al. A Novel Opto-Electromagnetic Actuator Coupled to the tympanic Membrane. J Biomech. Dec. 5, 2008;41(16):3515-8. Epub Nov. 7, 2008.
Lee, et al. The optimal magnetic force for a novel actuator coupled to the tympanic membrane: a finite element analysis. Biomedical engineering: applications, basis and communications. 2007; 19(3):171-177.
Levy, et al. Characterization of the available feedback gain margin at two device microphone locations, in the fossa triangularis and Behind the Ear, for the light-based contact hearing device. Acoustical Society of America (ASA) meeting, 2013 (San Francisco).
Levy, et al. Extended High-Frequency Bandwidth Improves Speech Reception in the Presence of Spatially Separated Masking Speech. Ear Hear. Sep.-Oct. 2015;36(5):e214-24. doi: 10.1097/AUD.0000000000000161.
Levy et al. Light-driven contact hearing aid: a removable direct-drive hearing device option for mild to severe sensorineural hearing impairment. Conference on Implantable Auditory Prostheses, Tahoe City, CA, Jul. 2017. 4 pages.
McElveen et al. Overcoming High-Frequency Limitations of Air Conduction Hearing Devices Using a Light-Driven Contact Hearing Aid. Poster presentation at The Triological Society, 120th Annual Meeting at COSM, Apr. 28, 2017; San Diego, CA.
Moore, et al. Spectro-temporal characteristics of speech at high frequencies, and the potential for restoration of audibility to people with mild-to-moderate hearing loss. Ear Hear. Dec. 2008;29(6):907-22. doi: 10.1097/AUD.0b013e31818246f6.
Perkins, et al. Light-based Contact Hearing Device: Characterization of available Feedback Gain Margin at two device microphone locations. Presented at AAO-HNSF Annual Meeting, 2013 (Vancouver).
Perkins, et al. The EarLens Photonic Transducer: Extended bandwidth. Presented at AAO-HNSF Annual Meeting, 2011 (San Francisco).
Perkins, et al. The EarLens System: New sound transduction methods. Hear Res. Feb. 2, 2010; 10 pages total.
Perkins, R. Earlens tympanic contact transducer: a new method of sound transduction to the human ear. Otolaryngol Head Neck Surg. Jun. 1996; 114(6):720-8.
Puria, et al. Cues above 4 kilohertz can improve spatially separated speech recognition. The Journal of the Acoustical Society of America, 2011, 129, 2384.
Puria, et al. Extending bandwidth above 4 kHz improves speech understanding in the presence of masking speech. Association for Research in Otolaryngology Annual Meeting, 2012 (San Diego).
Puria, et al. Extending bandwidth provides the brain what it needs to improve hearing in noise. First international conference on cognitive hearing science for communication, 2011 (Linkoping, Sweden).
Puria, et al. Hearing Restoration: Improved Multi-talker Speech Understanding. 5th International Symposium on Middle Ear Mechanics In Research and Otology (MEMRO), Jun. 2009 (Stanford University).
Puria, et al. Imaging, Physiology and Biomechanics of the middle ear: Towards understating the functional consequences of anatomy. Stanford Mechanics and Computation Symposium, 2005, ed Fong J.
Puria, et al. Sound-Pressure Measurements in The Cochlear Vestibule of Human-Cadaver Ears. Journal of the Acoustical Society of America. 1997; 101 (5-1): 2754-2770.
Puria, et al. Temporal-Bone Measurements of the Maximum Equivalent Pressure Output and Maximum Stable Gain of a Light-Driven Hearing System That Mechanically Stimulates the Umbo. Otol Neurotol. Feb. 2016;37(2):160-6. doi: 10.1097/MAO.0000000000000941.
Puria, et al. The EarLens Photonic Hearing Aid. Association for Research in Otolaryngology Annual Meeting, 2012 (San Diego).
Puria, et al. The Effects of bandwidth and microphone location on understanding of masked speech by normal-hearing and hearing-impaired listeners. International Conference for Hearing Aid Research (IHCON) meeting, 2012 (Tahoe City).
Puria. Measurements of human middle ear forward and reverse acoustics: implications for otoacoustic emissions. J Acoust Soc Am. May 2003; 113(5):2773-89.
Puria, S. Middle Ear Hearing Devices. Chapter 10. Part of the series Springer Handbook of Auditory Research pp. 273-308. Date: Feb. 9, 2013.
Song, et al. The development of a non-surgical direct drive hearing device with a wireless actuator coupled to the tympanic membrane. Applied Acoustics. Dec. 31, 2013;74(12):1511-8.
Struck, et al. Comparison of Real-world Bandwidth in Hearing Aids vs Earlens Light-driven Hearing Aid System. The Hearing Review. TechTopic: EarLens. Hearingreview.com. Mar. 14, 2017. pp. 24-28.

* cited by examiner

LIGHT DRIVEN CONTACT HEARING AID

CROSS REFERENCE TO RELATED APPLICATIONS

This application is a continuation of PCT application No. PCT/US2019/013822, filed Jan. 16, 2019, which claims priority to U.S. Provisional Application No. 62/620,341, filed Jan. 22, 2018, the contents of which are incorporated herein by reference in their entirety.

BACKGROUND OF THE INVENTION

Field of the Invention

The present invention is directed to a contact hearing aid system and, more particularly to a contact hearing system wherein the light beam emitted from the ear tip may be generated by more than one laser.

BACKGROUND

Light driven contact hearing aids use anatomical information derived from an individual's ear canal to custom build light emitting ear tips (emitters or light tips) which are positioned in the user's ear canal and lenses (receivers) which sit on the user's tympanic lens. In such hearing aids, the lens may include a photodetector and the anatomical information is used to, for example, ensure optical alignment between the light tip and the lens for efficient power and data transfer. In such hearing aids, it may be difficult to achieve and/or maintain optimal alignment between the emitter and the receiver for one or more of the following reasons: the anatomical representation used in manufacturing the emitter and/or receiver may not be accurate; the anatomical representation used in manufacturing the emitter and/or receiver may represent the shape of the ear canal in a position other than the position in which the hearing aid is normally used (e.g., the anatomical representation may be made with the user lying down while the hearing aid is normally used when the user in a sitting or standing); manufacturing tolerances may result in misalignment of components; placement of the ear tip in the ear canal may not be consistent with the location and registration to the anatomy assumed during manufacturing; or, the ear tip may move while in the canal, resulting in loss of alignment between the emitter and receiver. Prior art emitters, which rely on a single laser transmitting through a relatively narrow angle diffuser, have difficulty achieving and/or maintaining optimal coupling.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

DETAILED DESCRIPTION OF THE INVENTION

Figure 1:
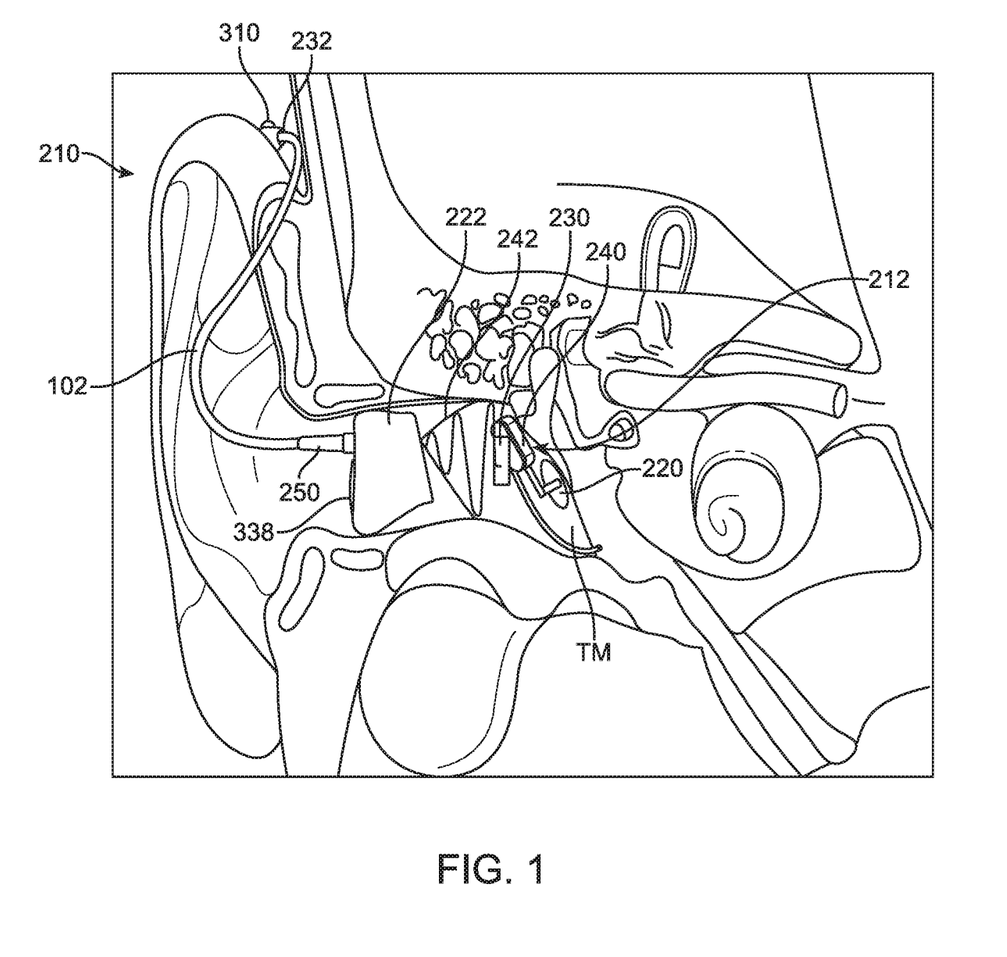
FIG. 1 is a cutaway view of an ear canal showing a contact hearing system for use in a method according to the present invention wherein at least a portion of the contact hearing system is positioned in the ear canal.

FIG. 1 is a cutaway view of an ear canal showing a contact hearing system 210 according to the present invention, wherein the contact hearing system 210 is positioned in the ear canal of a user. In embodiments of the invention, contact hearing system 210 may comprise a contact hearing system using light to transmit information and/or power from ear tip 222 to contact hearing device 212. In FIG. 1, contact hearing system 210 may further include audio processor 232, which audio processor may include at least one external microphone 310. Audio processor 232 may be connected to ear tip 222 by cable 102, which is adapted to transmit signals from audio processor 232 to ear tip 222. Taper tube 250 may be used to support cable 102 at ear tip 222. Ear tip 222 may further include an acoustic vent 338. Ear tip 222 may be a light tip which radiates light pulses 242 in response to signals from audio processor 232. Light or other signals radiated by ear tip 222 may be received by contact hearing device 212, which may comprise photodetector 230, microactuator 240, and umbo platform 220. In embodiments of the invention, ear tip 222 either alone or in combination with audio processor 232 may comprise an emitter, such as, for example emitter 108 which is described and illustrated herein. In embodiments of the invention, contact hearing device 212 may comprise a receiver.

Figure 2:
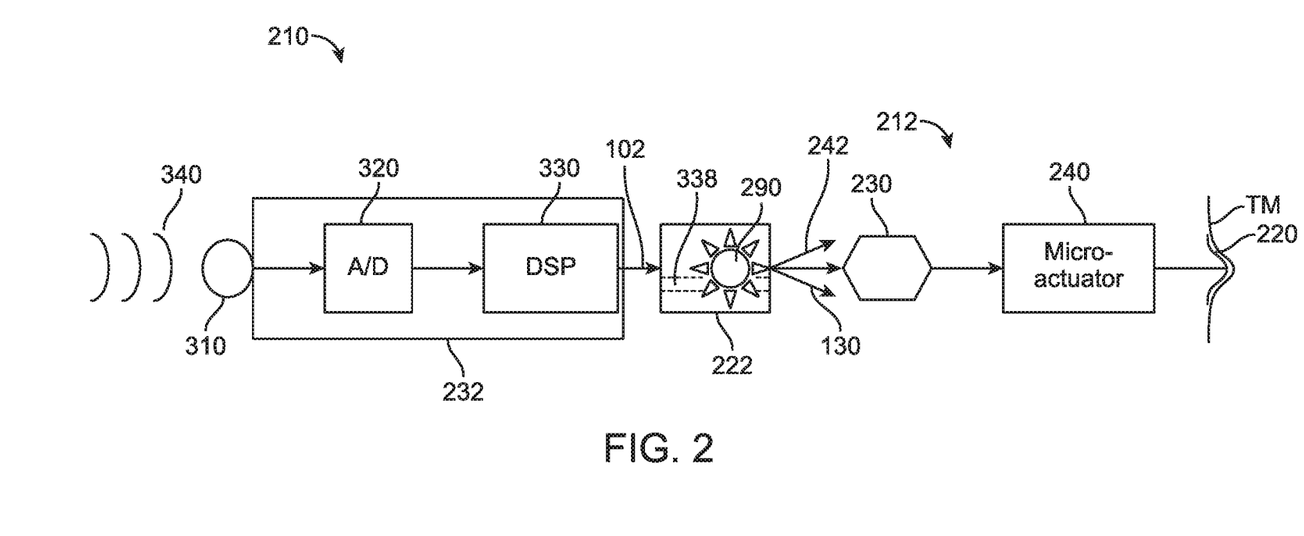
FIG. 2 is a block diagram of a contact hearing system according to the present invention.

FIG. 2 is a block diagram of a contact hearing system 210 for use in a method according to the present invention. In embodiments of the invention, contact hearing system 210 is positioned in the ear canal of a user. In FIG. 2, ambient sound 340 may be received by external microphone 310 of audio processor 232, which then processes the received sound by passing it through processing circuitry, which may include analog to digital converter 320 and digital signal processor 330. The output of audio processor 232 may be transmitted to an ear tip 222 by cable 102. Signals transmitted to ear tip 222 may then be transmitted to contact hearing device 212 by, for example, causing light source 290 to radiate light pulses 242. In embodiments of the invention, contact hearing device 212 may include photodetector 230, microactuator 240, and umbo lens 220. Light pulses 242 received by photodetector 230 may be transmitted to microactuator 240, moving umbo lens 220, generating tympanic membrane motion which is perceived by the user as sound.

In embodiments of the invention, the signal transmitted to ear tip 222 may be a signal representative of the audio signal detected by microphone 310, which may then be transmitted to contact hearing device 212. In embodiments of the invention, the signal transmitted to ear tip 222 may be a control signal configured to cause the vibration of the tympanic membrane.

Figure 3:
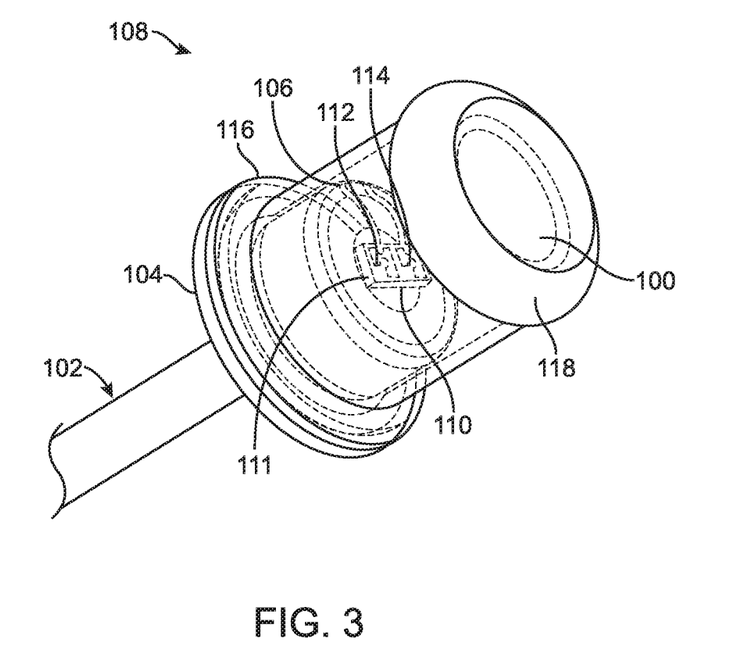
FIG. 3 is a perspective view of a multi-laser emitter for use in a contact hearing system according to the present invention.

FIG. 3 is a perspective view of a multi-laser emitter 108 according to the present invention. Emitter 108 may include a plurality of lasers 111 and a diffuser 100. In one embodiment of the invention, diffuser 100 may be a lens or other transparent window which diffuses light in a controlled way. In one embodiment of the invention, emitter 108 may include first laser 112 and second laser 114. Emitter 108 may further include emitter housing 116, laser drive wires 106, substrate 110, and diffuser housing 118. Emitter 108 may be connected to cable 102. In one embodiment, laser drive wires 106 pass through cable 102 and into emitter 108, where they are connected to lasers 111 on substrate 110. Lasers 111 are positioned on substrate 110 to radiate out of emitter 108 through diffuser 100.

Figure 4:
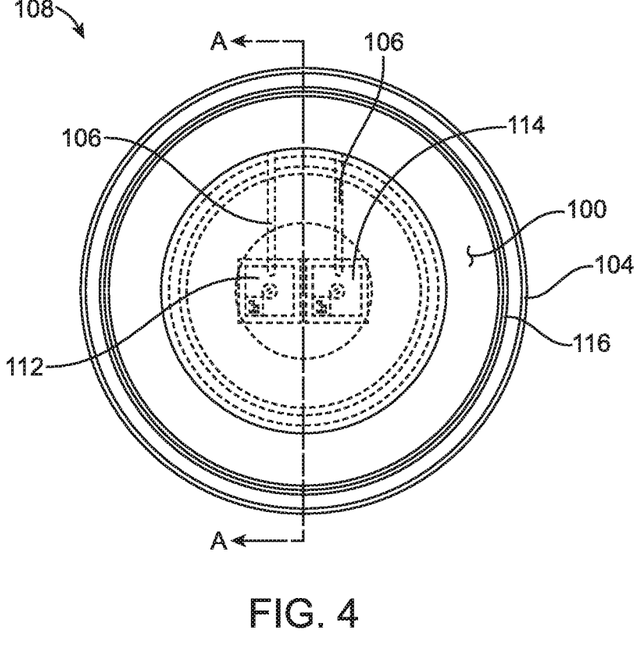
FIG. 4 is an end view of a multi-laser emitter for use in a contact hearing system according to the present invention.

FIG. 4 is an end view of a multi-laser emitter 108 according to the present invention. In the embodiment of FIG. 4, emitter 108 is a multi-light source emitter, including a first laser 112 and a second laser 114. Laser's 112 and 114 are positioned in emitter housing 116, which includes emitter housing flange 104 and diffuser 100. Lasers 112 and 114 are further connected to laser drive wires 106 which provide drive signals for lasers 112 and 114.

Figure 5:
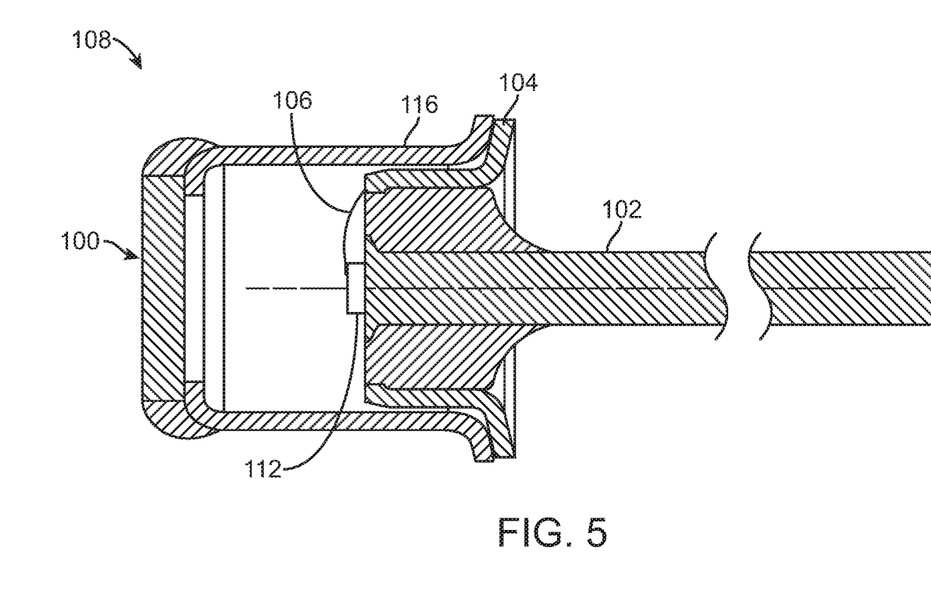
FIG. 5 is a side cutaway view of a multi-laser emitter for use in a contact hearing system according to the present invention.

FIG. 5 is a side cutaway view of a multi-laser emitter 108 according to the present invention. The view of FIG. 5 is taken along AA of FIG. 4. In FIG. 5, laser 112 is positioned in emitter housing 116 which further includes emitter housing flange 104 and diffuser 100. Laser 112 is further connected to laser drive wire 106, which extends through cable 102.

Figure 6:
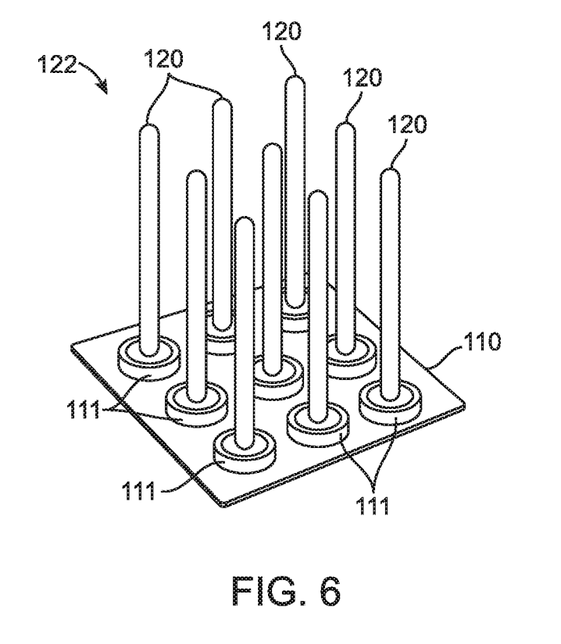
FIG. 6 is a perspective view of a multi-laser array for use in a contact hearing system according to the present invention.

FIG. 6 is a perspective view of a multi-laser array 122 for use in the present invention. In laser array 122, multiple lasers, for example VCSEL lasers, may be positioned on a single substrate 110. In FIG. 6, each laser 111 is shown radiating a light beam 120, which may be a collimated light beam.

Figure 7:
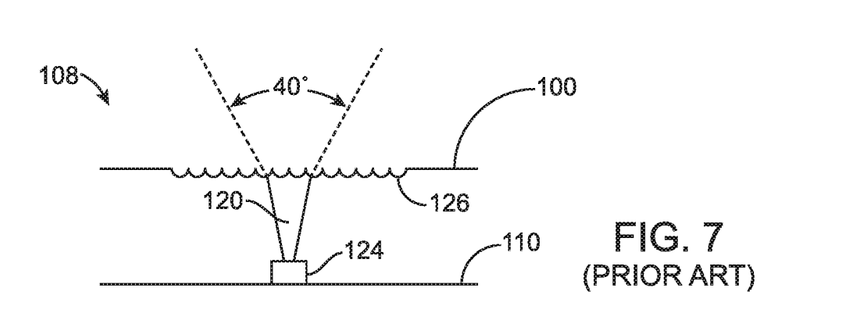
FIG. 7 illustrates a single light source emitter in a contact hearing system according to the prior art wherein the light is radiated through a diffuser.

FIG. 7 illustrates a single light source emitter such as those found in the prior art, wherein the light from light source 124 is radiated through a narrow angle (e.g., 40 degrees of diffusion) diffuser 100. In the prior art, diffuser 100 was designed such that light radiating from emitter 108 will have a relatively narrow diffusion angle of approximately 40 degrees. In FIG. 7, diffuser 100 may be a flat diffuser which incorporates micro elements 126, wherein micro elements 126 provide the required diffusion. Micro elements 126 may be, for example, convex features in the surface of diffuser 100. In FIG. 7, light source 124 is a laser which radiates light beam 120, which is a beam of collimated light.

Figure 8:
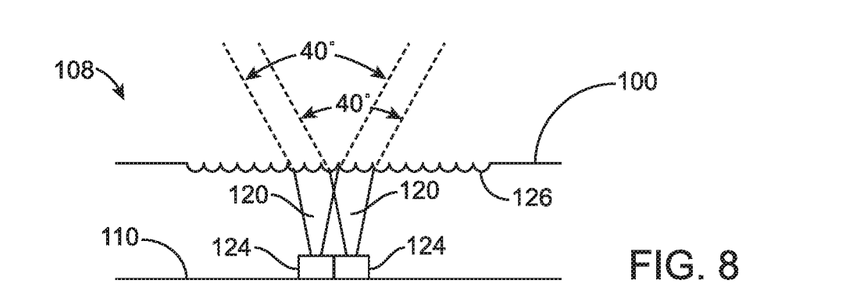
FIG. 8 illustrates a multi light source emitter according to the present invention wherein the light is radiated through a diffuser.

FIG. 8 illustrates a dual light source emitter 108 according to the present invention wherein the light from multiple light sources 124 is radiated through diffuser 100. In embodiments of the invention, light sources 124 may be laser sources and light beams 120 may be beams of collimated light. In embodiments of the invention, diffuser 100 may be designed to have a relatively narrow diffuser angle of approximately 40 degrees and the combined output from sources 124 may be diffused such that the angle covered by the output from diffuser 100 covers an angle of greater than the 40 degree diffusion angle of diffuser 100, with the total diffusion angle depending upon the separation between light sources 124.

Figure 9:
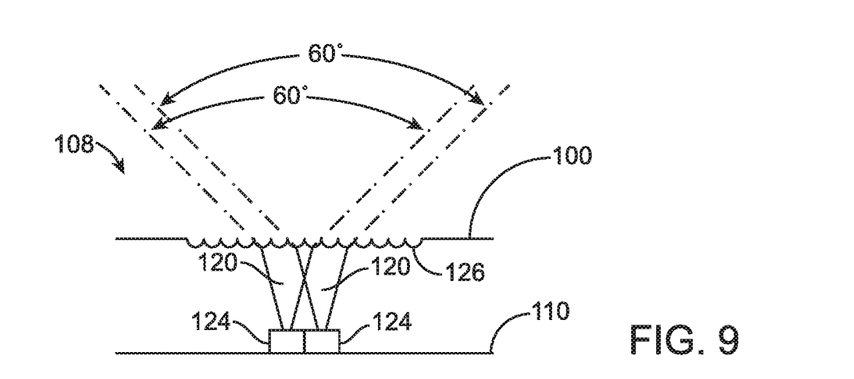
FIG. 9 illustrates a multi light source emitter according to the present invention wherein the light is radiated through a diffuser.

FIG. 9 illustrates a dual light source emitter 108 wherein the light from multiple light sources 124 is radiated through diffuser 100. In embodiments of the invention, light sources 124 may be laser sources and light beams 120 may be beams of collimated light. In embodiments of the invention, diffuser 100 may be designed to have a relatively wide diffuser angle of approximately 60 degrees and the combined output from sources 124 may be diffused such that the angle covered by the output from diffuser 100 covers an angle of greater than the 60 degree diffusion angle of diffuser 100 with the total diffusion angle depending upon the separation between light sources 124.

Figure 10:
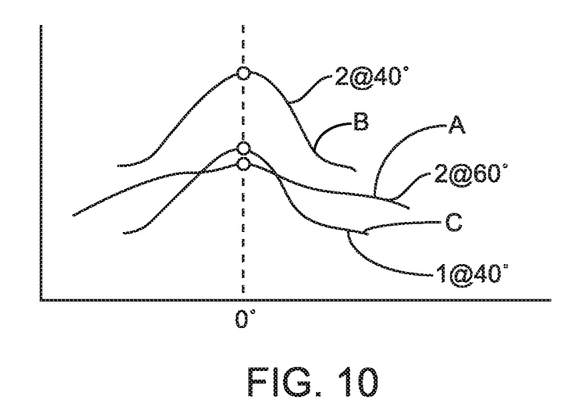
FIG. 10 is a graph of the output of different emitters, including emitters according to embodiments of the present invention.

FIG. 10 is a graph of the output of different emitters, including emitters according to embodiments of the present invention. In FIG. 10, plot A illustrates the output of a prior art emitter utilizing a single light source and a diffuser providing a 40 degree diffusion angle. Plot B illustrates the output of a dual light source emitter utilizing a diffuser providing a 40 degree diffusion angle. Plot C illustrates a dual light source emitter utilizing a diffuser which provides a 60 degree diffusion angle. As illustrated in the graphs of FIG. 10, a dual light source emitter utilizing a diffuser which provides a 60 degree diffusion angle will provide a peak output which is substantially the same as a single light source emitter with a 40 degree diffuser, while providing a substantially level output across a large area (much larger than the single diffuser alone), thereby enhancing the ability of the emitter to couple with the receiver and to stay coupled even when the emitter and receiver are not optimally aligned and/or the ear canal is moving.

In embodiments of the invention, two light sources provide more intensity utilizing the same input voltage. In these embodiments, the current draw will increase (e.g., two light sources may require up to twice the current of a single source). However, the use of multiple light sources is advantageous because of the increased output for the same input voltage since hearing aids are normally driven by a fixed voltage source (e.g., a battery).

In embodiments of the invention wherein multiple light sources are used, the diffusion angle may be increased to provide a broader output beam without reducing the intensity of the output, especially at the center of the beam. The use of multiple light sources also results in a flatter output intensity across the diffusion angle, resulting in a more uniform output. In one embodiment, two light sources and a doubling of the current will increase the peak output by 5 dB over a single light source at a 40 degree diffusion angle, however, if the diffusion angle is increased to 60 degrees, the 5 dB of gain is lost but the output is flatter and extends over the larger diffusion angle, increasing the likelihood of effective coupling between the emitter and the receiver. A wide diffusion angle (e.g., 60 degrees) may also be preferable to a more narrow diffusion angle (e.g., 40 degrees) because there is less sensitivity to motion in the ear canal which causes relative movement of the emitter and the receiver (e.g., jaw motion or swallowing motion). In embodiments of the invention, it may also be possible to increase the maximum drive voltage to increase the output over the diffusion angle.

Figure 11:
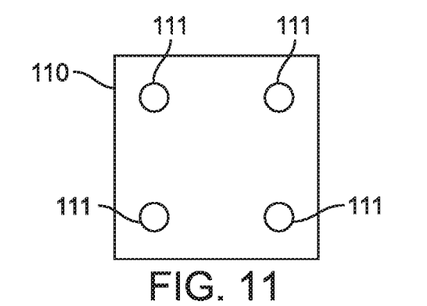
FIG. 11 is an illustration of a four laser substrate for use in a contact hearing aid according to the present invention.
Figure 12:
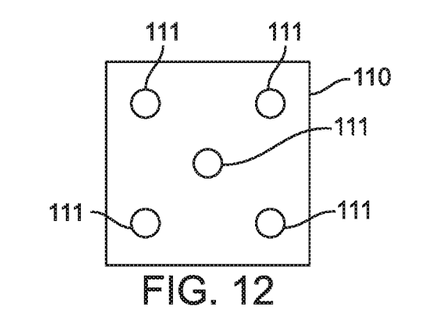
FIG. 12 is an illustration of a five laser substrate for use in a contact hearing aid according to the present invention.

FIG. 11 is an illustration of a four laser substrate 110 for use in an emitter according to the present invention. FIG. 12 is an illustration of a five laser substrate 110 for use in an emitter according to the present invention. In FIGS. 11 and 12, lasers 111, which may be VIXSEL lasers, are positioned on substrate 110. In embodiments of the invention, multi-laser substrates 110 may be incorporated into emitter 108.

Figure 13:
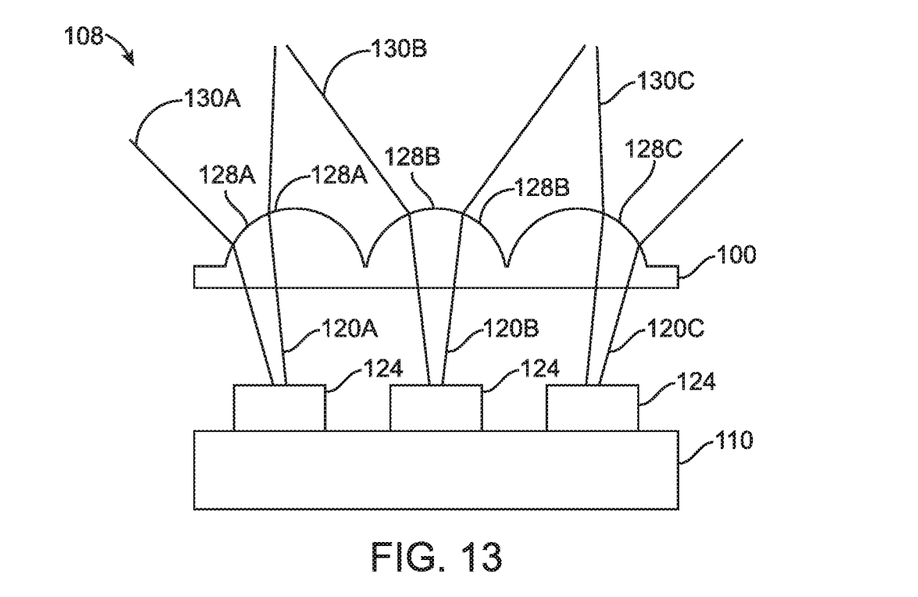
FIG. 13 is an illustration of a multi light source emitter according to one embodiment of the present invention.

FIG. 13 is an illustration of a multi light source emitter 108 according to one embodiment of the invention. In the embodiment of FIG. 13, multi light source emitter 108 may include diffuser 100 having convex features 128 on its surface wherein light hitting convex feature 128, such as, for example light beam 120, is diffused and directionally aligned according to the place on convex feature 128 where the light beam is incident. For example, light beam 120B is incident on the central region of convex feature 128B, resulting in an output beam 130B which is diffused but radiates in a direction substantially orthogonal to the surface of substrate 110. As a further example, light beam 120A is incident on a region of convex feature 120A which results in an output beam 130A which is diffused and radiates in a direction away from output beam 130B. As a further example, light beam 120C is incident on a region of convex feature 128C which results in an output beam 130C which is diffused and radiates in a direction away from output beam 130B and 130A.

Figure 14:
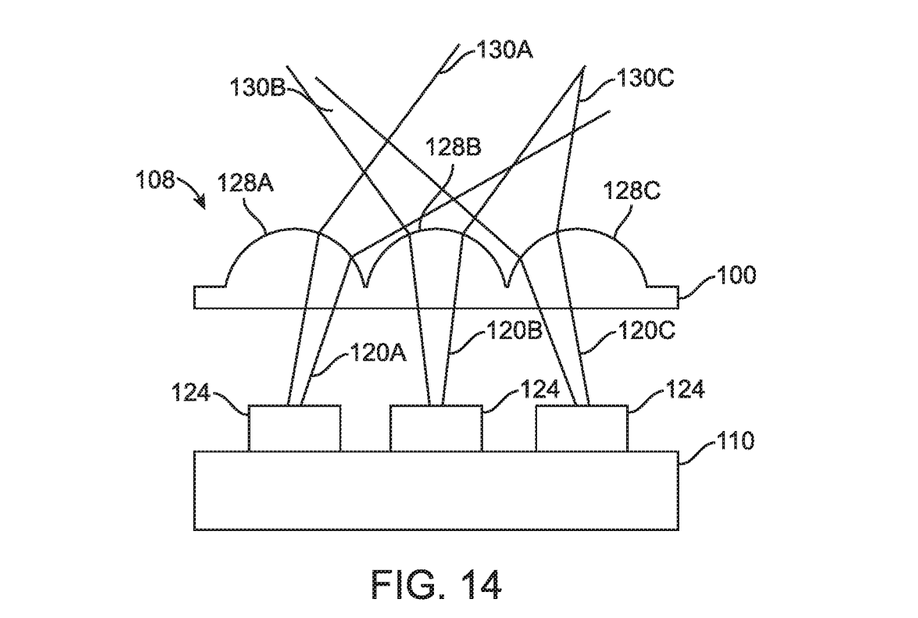
FIG. 14 is an illustration of a multi light source emitter according to one embodiment of the present invention.

FIG. 14 is an illustration of a multi light source emitter according to one embodiment of the invention. In the embodiment of FIG. 14, multi light source emitter 108 may include diffuser 100 having convex features 128 on its surface wherein light hitting convex feature 128, such as, for example light beam 120, is diffused and directionally aligned according to the place on convex feature 128 where the light beam is incident. For example, light beam 120B is incident on the central region of convex feature 128B, resulting in an output beam 130B which is diffused but radiates in a direction substantially orthogonal to the surface of substrate 110. As a further example, light beam 120A is incident on a region of convex feature 128A which results in an output beam 130A which is diffused and radiates in a direction toward output beam 130B. As a further example, light beam 120C is incident on a region of convex feature 128C which results in an output beam 130C which is diffused and radiates in a direction toward output beam 130B and 130A.

In embodiments of the invention, components of emitter 108 as illustrated in FIGS. 13 and 14 may be movable relative to one another such that the direction of output beam 130 may be modified by moving those components either together or relative to each other. In one embodiment of the invention, diffuser 100 may be movable relative to light sources 124, resulting in modified diffusion patterns as diffuser 100 is moved relative to light sources 124. In one embodiment, substrate 110, including light sources 124, may be moveable relative to diffuser 100, resulting in a modified diffusion pattern as substrate 110 is moved relative to diffuser 100. In one embodiment, light sources 124 may be moveable individually or in groups relative to substrate 110 and/or to diffuser 100, resulting in modified diffusion patterns as light sources 124 are moved relative to substrate 110 and/or to diffuser 100. In embodiments of the invention, the relative movement of the components of emitter 108 may be used to create outputs with diffusion patterns and directionality which optimize coupling between the emitter 108 and the receiver. In embodiments of the invention, the intensity of the signal received at the receiver may be measured and used by emitter 108 to adjust the relative position of the components of emitter 108 to optimize coupling between emitter 108 and the receiver. In embodiments of the invention, the coupling may be continuously optimized to compensate for relative movement between the emitter and receiver resulting from, for example, movement of the ear canal or anatomical components thereof as a result of actions by the user (e.g. swallowing or smiling). The coupling may, therefore, be continuously adjusted to maintain optimal coupling between the emitter and receiver.

Figure 15:
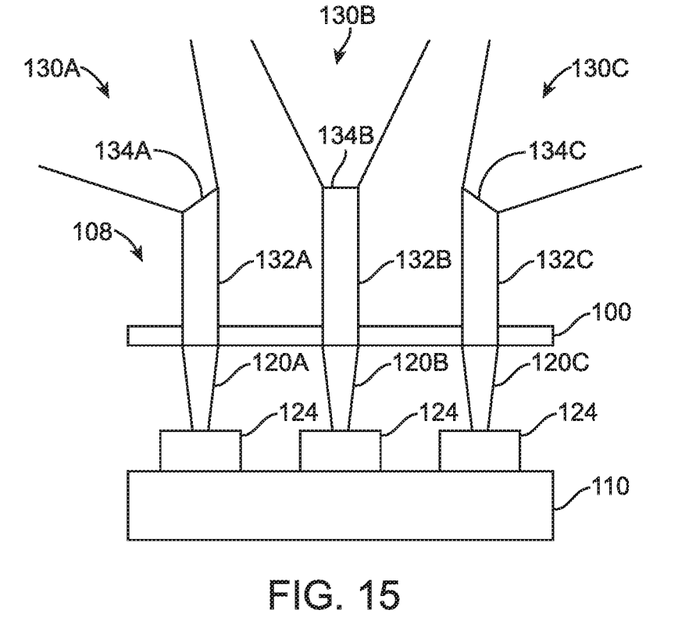
FIG. 15 is an illustration of a multi light source emitter according to one embodiment of the present invention.

FIG. 15 is an illustration of a multi light source emitter according to one embodiment of the invention. In the embodiment of FIG. 15, multi light source emitter 108 may include diffuser 100 having light tubes 132 on its surface wherein light hitting light tubes 132, such as, for example light beam 120, is diffused and directionally aligned according to the direction of the bevel surface 134 at the end of light tube 132. For example, light beam 120B is transmitted through light tube 132B to bevel surface 134B. Since bevel surface 134B is orthogonal to the axis of light tube 132B, output beam 130B, which is diffused, radiates in a direction substantially orthogonal to the surface of substrate 110. As a further example, light beam 120A is incident on light tube 132A which has a beveled surface 134A which is angled away from light tube 132B, resulting in an output beam 130A which is diffused and radiates in a direction away from output beam 130B. As a further example, light beam 120C is incident on light tube 132C which has a beveled surface 134C which is angled away from light tube 132B, resulting in an output beam 130C which is diffused and radiates in a direction away from output beam 130B and 130A.

Figure 16:
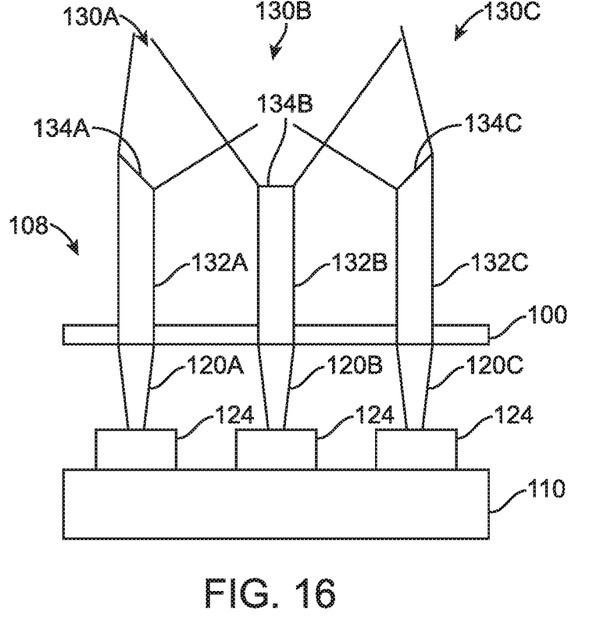
FIG. 16 is an illustration of a multi light source emitter according to one embodiment of the present invention.

FIG. 16 is an illustration of a multi light source emitter according to one embodiment of the invention. In the embodiment of FIG. 16, multi light source emitter 108 may include diffuser 100 having light tubes 132 on its surface wherein light hitting light tubes 132, such as, for example light beam 120, is diffused and directionally aligned according to the direction of the bevel surface 134 at the end of light tube 132. For example, light beam 120B is transmitted through light tube 132B to bevel surface 134B. Since bevel surface 134B is orthogonal to the axis of light tube 132B, output beam 130B, which is diffused, radiates in a direction substantially orthogonal to the surface of substrate 110. As a further example, light beam 120A is incident on light tube 132A which has a beveled surface 134A which is angled toward light tube 132B, resulting in an output beam 130A which is diffused and radiates in a direction toward output beam 130B. As a further example, light beam 120C is incident light tube 132C which has a beveled surface 134C which is angled toward light tube 132B, resulting in an output beam 130C which is diffused and radiates in a direction toward output beam 130B and 130A.

Embodiments of the present invention include light driven hearing aids wherein the emitter of the hearing aid includes more than one laser. In embodiments of the invention, the laser used in the emitter may be a vertical-cavity surface-emitting laser or VCSEL, which is a type of semiconductor laser diode wherein the laser beam is emitted perpendicular to the top surface of the laser. In embodiments of the invention, the emitter may be a multi-VCSEL laser array. In embodiments of the invention, the present invention describes a method of electronically steering the light beam of a contact hearing aid system, to achieve more optimal optical alignment between the emitter and the receiver. In embodiments of the invention, the array can comprise of a number of VCSELs (or other light sources) which can be integrated into a single light component. The light component may be used in the construction of the ear tip and provides electrical connections to the BTE Processor with the use of electrical wires which run inside the eartip cable.

In embodiments of the invention, the processor houses a power source, a charging mechanism, an audio processing means, microphones, control buttons, radio circuitry and a cable connector. The cable connector may support sufficient number of electrical wires to connect the processor to each VCSEL element on the Light tip. In embodiments of the invention, the processor may further include electronic multiplexing means to electronically choose one of many VCSELs to activate at a given time and software to control the multiplexing. In embodiments of the invention, control may be provided through buttons on the BTE Processor and/or through commands received from an external source such as a smartphone.

In embodiments of the invention, the ear tip cable houses multiple strands of electrical wire which may be stranded with (e.g., Kevlar) support wires. The electrical wires may be individually insulated electrically and may be housed in PEBAX or a similar polymer housing. The ear tip cable may be connected to the processor by a connector, where the connector includes a sufficient number of conductors to connect to the processor to the light tip. The light tip may include a permanent connection or a separate connector.

In embodiments of the invention, the ear tip/light tip houses a custom shell made to comply with an individual ear canal anatomy. At the distal end (medial to the ear canal when in situ) it houses a "light component". It can include vent holes as desired. In embodiments of the invention, the ear tip/light tip may comprise a non-custom shell made to comply with a range of ear canal anatomies. At the distal end (medial to the ear canal when in situ) the non-custom shall houses a "light component". It can include vent holes as desired. The selection of the emitter can be optimized once the non-custom shell is positioned in a location that is most stable and comfortable for the ear canal anatomy being fitted.

The light component as used herein, may comprise an array of VCSELs formed on a common substrate to form the electrical ground or return connection. Each VCSEL may be wire bonded to an electrical contact on a substrate where the ear tip cables make electrical connection to the electrical contact. Furthermore, the VCSEL array may be bonded to a custom shaped optical lens, which projects the beam of its corresponding VCSEL at a certain direction. The beam so formed may, in one embodiment, provide overlapping circles when shone on a flat surface at a distance away from the light component. In embodiments of the invention, the optical lens may have anti reflective coating at the inside surface.

In embodiments of the invention, the BTE processor may include a multiplexer which electrically connects an audio switching waveform generated using, for example, pulse density multiplexing to one VCSEL at a time. When connected to an individual VCSEL is driven with the signal and is connected to a common ground. As an example an array of five VCSELs can generated five different beams using six conductor (five signal and one ground) between the BTE Processor and Light Tip.

In embodiments of the invention, a method is describe herein whereby the light beam emitted by the light tip can be electronically steered by switching among a number of VCSELs and their corresponding optical lenses in the light component and thereby changing the angle and alignment of the beam. In one embodiment, the light beam may be steered by the user by pressing buttons on the Processor, which can cycle through different beams, much like the volume control function, until the user is happy with sound quality. In an alternative embodiment, the light beam may be steered using, for example, a smartphone app, where the user interface commands will be wirelessly sent to the processor and result in cycling of available VCSEL beams until the user is satisfied with the sound quality.

In one embodiment of the invention, a multi-light source emitter may be used to radiate at least two separate beams from an ear tip into the ear canal of the user. In this embodiment, the hearing aid may have a set up mode, wherein the light sources are selectively turned on and a feedback signal associated with the degree of coupling between the emitter and receiver for the selected light source is measured. The light source, or combination of light sources which provide the best coupling may then be selected and that combination used for that user. In one embodiment, the feedback may be audible feedback resulting from the signal creating motion of the tympanic membrane. In the embodiment of the invention wherein audible feedback is used, the ear tip may include a microphone, e.g., an in the ear canal microphone, to pick up and measure the audible feedback. In one example, the feedback may be a signal transmitted from the receiver to the emitter, wherein the feedback signal is representative of the strength of the signal incident upon the receiver photodetector. In embodiments of the invention, the transmitted signal may be a high power pure tone signal, such as, for example, a signal which generates a 10 KHz modulation of the tympanic membrane.

In embodiments of the invention, the system would scan through the light sources one at a time to provide the one that had the optimal coupling. In embodiments of the invention, the individual light sources radiated from the emitter may radiate in different directions and/or have differing diffusion angles. In embodiments of the invention, the system may select more than one light source to use during normal signal transmission in order to obtain optimal coupling.

In one embodiment of the invention, the beam steering/beam selection, may occur each time the hearing aid is turned on to ensure that the emitter maintains optimal coupling with the receiver. In embodiments of the invention, beam steering/beam selection may occur at selected intervals to ensure that the emitter maintains optimal coupling with the receiver.

In one embodiment, coupling between the emitter and receiver refers to the percentage of light energy radiated from the emitter which actually reaches the receiver and is turned into electrical energy by the photodetector. In embodiments of the invention, there is a tradeoff between the amount of power used by the emitter, which is desirably maintained at a low level to reduce battery drain, and the number of light sources which may be used to ensure optimal coupling between the emitter and receiver. Therefore, it may be advantageous to limit the number of light sources used by the emitter while achieving the best possible coupling between the emitter and receiver.

In embodiments of the invention, the beam scanning/beam selection may be conducted at a high power and the signal/power transmission at a low or intermediate power setting. The degree of coupling achieved by the selected light source(s) will impact the power needed to transmit the signal to the receiver without loss of information. The better the coupling, the less energy the signal will need.

In embodiments of the invention, the beam scanning/beam selection (aka calibration mode) may be accomplished with a 100% duty cycle while the signal transmission (aka latch mode) may be accomplished with a 50%, or less, duty cycle. In embodiments of the invention, when the hearing aid is in the beam scanning/beam selection mode it may be referred to as being in the calibration mode. In embodiments of the invention, once the hearing aid has established optimal coupling between the emitter and receiver, it may begin signal transmission, at which point it may be said to be in the latch mode.

In embodiments of the invention, the multiple light sources may be laser light sources, such as VCSEL lasers, which may be independent or integrated onto a single substrate.

In embodiments of the invention, the diffuser may be arranged such that the light from each light source is diffused differently, for example at a different diffusion angle and/or at a different direction from the emitter. By allowing individual light sources to be diffused at different diffusion angles and/or different directions, the coupling efficiency may be maintained even when the ear tip moves in the canal, increasing the robustness of the connection, which results in less sound variability for the user.

In embodiments of the invention, individual light sources may be used for different purposes. For example, one light source may be used to transmit power to the receiver while a second light source may be use to transmit data (e.g., sound data) to the receiver. In embodiments of the invention, the light sources may have differing wavelengths.

In one embodiment of the invention, the power being transmitted to the receiver may be monitored by including a second emitter in the receiver (e.g., attached to the photodetector). The second emitter may be used to transmit a signal back to the first emitter (the ear tip), which provides feedback on the amount of power reaching the photodetector. This feedback may then be used by the system to select the light source or plurality of light sources which provide the best coupling between the first emitter and the receiver. This signal may also be used to provide an indication of when the coupling is lost or degraded by, for example, movement of the emitter (ear tip) in the ear canal of the user. The primary emitter may move in the ear canal for a number of reasons, including: movement by the user to facilitate comfortable placement, changes resulting from the ear tip being removed and replaced (e.g., at night and in the morning); chewing; smiling; or swallowing. When the power received at the receiver (e.g., photodetector) drops as a result of any of those movements, the receiver may notify the emitter and the hearing aid may go through a recalibration to select the light source and/or light source diffuser combination which results in the best coupling between the emitter output and the receiver.

In embodiments of the invention, the light beams may be electronically steered to achieve more optimal optical alignment between the emitter and the receiver. In embodiments of the invention, the light beam width may be adjusted to enhance coupling between the emitter and the receiver. In embodiments of the invention, the light beam direction may be made adjustable while the ear tip is in-situ using, for example, multiple lasers in the emitter and/or electronic beam steering circuitry in the emitter.

Embodiments of the present invention include a hearing aid system including an emitter, wherein the emitter includes a diffuser and at least two light sources. Embodiments of the hearing aid system may further include a receiver, wherein the receiver comprises at least one photodetector and a microactuator. Embodiments of the hearing aid system may further include a hearing aid system wherein the light sources comprise lasers. Embodiments of the hearing aid system may further include a hearing aid system wherein the light sources comprise VCSEL lasers. Embodiments of the hearing aid system may further include a hearing aid system wherein the diffuser diffuses light from the at least two sources at an angle of greater than approximately 50 degrees. Embodiments of the hearing aid system may further include a hearing aid system wherein the diffuser diffuses light from the at least two sources at an angle of greater than approximately 30 degrees. Embodiments of the hearing aid system may further include a hearing aid system wherein a first of the at least two light sources is on a first side of the emitter and the second of the at least two light sources is on a second side of the emitter. Embodiments of the hearing aid system may further include a hearing aid system wherein a centerline runs through the emitter, the first light source being positioned on a first side of the centerline and the second light source being positioned on a second side of the light source.

Embodiments of the present invention include a method of selecting at least one light source from a plurality of light sources in an emitter of a hearing aid system, the method including the steps of: driving each light source of the plurality and measuring a feedback signal; and selecting the light source which provides the feedback signal having the largest magnitude. Embodiments of a method according to the present invention further include a step of selecting a second light source by selecting the light source which creates the feedback signal having the second largest magnitude. Embodiments of a method according to the present invention further include a method wherein the selected light source is used to transmit information to the receiver. Embodiments of a method according to the present invention further include a method wherein the selected light source is used to transmit power to the receiver. Embodiments of a method according to the present invention further include a method wherein the feedback signal is an audio feedback signal. Embodiments of a method according to the present invention further include a method wherein the feedback signal is an electronic feedback signal.

Embodiments of a method according to the present invention further include A method of transmitting information from an emitter to a receiver in a hearing aid, the method including the steps of: radiating light energy from at least two light sources in the emitter; diffusing the radiated light energy using a diffuser at an output of the emitter; and, redirecting the radiated light energy as it passes through the diffuser. Embodiments of a method according to the present invention further include a method wherein the light energy from a first light source is redirected in a first direction and the light energy from a second light source is redirected in a second direction. Embodiments of a method according to the present invention further include a method wherein the first direction is away from the second direction. Embodiments of a method according to the present invention further include a method wherein the first direction is toward the second direction. Embodiments of a method according to the present invention further include a method wherein the first direction is substantially orthogonal to a substrate on which the light source is mounted. Embodiments of a method according to the present invention further include a method wherein the first direction is substantially orthogonal to the output surface of the diffuser.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth hereinbelow not be construed as being order-specific unless such order specificity is expressly stated in the claim.

| REFERENCE NUMBERS | |
|---|---|
| Number | Element |
| 100 | Diffuser |
| 102 | Cable |
| 104 | Emitter Housing Flange |
| 106 | Laser Drive Wires |
| 108 | Emitter |
| 110 | Substrate |
| 111 | Laser |
| 112 | $1^{st}$ Laser |
| 114 | $2^{nd}$ Laser |
| 116 | Emitter Housing |
| 118 | Diffuser Housing |
| 120 | Light Beam (Collimated) |
| 122 | Laser Array |
| 124 | Light Source |
| 126 | Micro-Elements |
| 128 | Convex Features |
| 130 | Output Beam |
| 132 | Light Tubes (optical fibers) |
| 134 | Bevel Surface |
| 210 | Contact Hearing System |
| 212 | Contact Hearing Device |
| 222 | Ear Tip |
| 230 | Photodetector |
| 232 | Audio Processor |
| 240 | Microactuator |
| 242 | Light Pulses |
| 220 | Umbo Lens |
| 250 | Taper Tube |
| 290 | Light Source |
| 310 | External Microphone |
| 320 | Analog to Digital Converter |
| 330 | Digital Signal Processor |
| 338 | Acoustic Vent |
| 340 | Acoustic Input (Audible Sound) |
| 342 | Acoustic Feedback |
| TM | Tympanic Membrane |

The invention claimed is:

1. A hearing aid system comprising:
   a multi-laser emitter, wherein the multi-laser emitter includes at least a first laser source positioned on a substrate and a second laser source positioned on the substrate with a configured separation distance between the first and second laser sources, and wherein the multi-laser emitter further includes a diffuser having a configured diffusion angle and positioned away from the first and second laser sources; and
   a receiver, wherein the receiver comprises at least one photodetector and a microactuator, the at least one photodetector configured to receive a combined multi-laser output signal based on diffusion by the diffuser of a first laser beam from the first laser source and a second laser beam from the second laser source, wherein the combined multi-laser output signal has a total diffusion angle that is greater than the configured diffusion angle of the diffuser and is based at least in part on the configured separation distance between the first and second laser sources.

2. The hearing aid system according to claim 1 wherein the first and second laser sources comprise vertical-cavity surface-emitting laser (VCSEL) lasers.

3. The hearing aid system according to claim 1 wherein the diffuser diffuses light from the first and second laser sources with the configured diffusion angle being equal to an angle of greater than approximately 50 degrees.

4. The hearing aid system according to claim 1 wherein the diffuser diffuses light from the first and second laser sources with the configured diffusion angle being equal to an angle of greater than approximately 30 degrees.

5. The hearing aid system according to claim 1 wherein the first laser source is on a first side of the multi-laser emitter and the second laser source is on a second side of the multi-laser emitter.

6. The hearing aid system according to claim 5 wherein a centerline runs through the multi-laser emitter, the first laser source being positioned on a first side of the centerline and the second laser source being positioned on a second side of the centerline.

7. A method of selecting at least one laser source from a plurality of laser sources in a multi-laser emitter of a hearing aid system, the method comprising:
   driving each laser source of the plurality of laser sources, wherein the plurality of laser sources includes at least a first laser source positioned on a substrate and a second laser source positioned on the substrate with a configured separation distance between the first and second laser sources, and wherein the multi-laser emitter further includes a diffuser having a configured diffusion angle and positioned away from the first and second laser sources;
   measuring a feedback signal based on receiving a combined multi-laser output signal using at least one photodetector of a receiver of the hearing aid system, wherein:
      the at least one photodetector is configured to receive the combined multi-laser output signal based on diffusion by the diffuser of a first laser beam from the first laser source and a second laser beam from the second laser source; and
      a total diffusion angle associated with the combined multi-laser output signal is greater than the configured diffusion angle of the diffuser, the total diffusion angle based at least in part on the configured separation distance between the first and second laser sources; and
   selecting, from the plurality of laser sources, a respective laser source which provides the feedback signal having the largest magnitude.

8. The method according to claim 7 wherein the method further includes the step of selecting an additional laser source from the plurality of laser sources by selecting the laser source which creates the feedback signal having the second largest magnitude.

9. The method according to claim 7 wherein the respective laser source selected from the plurality of laser sources is used to transmit information to the receiver of the hearing aid system, wherein the receiver comprises the at least one photodetector and a microactuator.

10. The method according to claim 9 wherein the respective laser source selected from the plurality of laser sources is used to transmit power to the receiver.

11. The method according to claim 7 wherein the feedback signal is an audio feedback signal.

12. The method according to claim 7 wherein the feedback signal is an electronic feedback signal.

13. A method of transmitting information from a multi-laser emitter to a receiver in a hearing aid, the method comprising:
radiating light energy from at least two laser sources in the multi-laser emitter;
diffusing the radiated light energy using a diffuser at an output of the multi-laser emitter; and
redirecting the radiated light energy as it passes through the diffuser, wherein the radiated light energy has a total diffusion angle that is greater than a configured diffusion angle of the diffuser and is based at least in part on a configured separation distance between the at least two laser sources.

14. The method according to claim 13 wherein:
the at least two laser sources includes a first laser source and a second laser source;
the light energy from the first laser source is redirected in a first direction; and
the light energy from the second laser source is redirected in a second direction.

15. The method according to claim 14 wherein the first direction is away from the second direction.

16. The method according to claim 14 wherein the first direction is toward the second direction.

17. The method according to claim 14 wherein the first direction is substantially orthogonal to a substrate on which the at least two laser sources are mounted.

18. The method according to claim 14 wherein the first direction is substantially orthogonal to an output surface of the diffuser.

* * * * *